(12) United States Patent
Sigalas et al.

(10) Patent No.: US 7,696,477 B2
(45) Date of Patent: Apr. 13, 2010

(54) ELECTRIC-FIELD-ENHANCEMENT STRUCTURES INCLUDING DIELECTRIC PARTICLES, APPARATUS INCLUDING SAME, AND METHODS OF USE

(75) Inventors: Mihail Sigalas, Santa Clara, CA (US); R. Stanley Williams, Redwwod City, CA (US); David A. Fattal, Mountain View, CA (US); Shih-Yuan Wang, Palo Alto, CA (US); Raymond G. Beausoleil, Redmond, WA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 515 days.

(21) Appl. No.: 11/724,409

(22) Filed: Mar. 14, 2007

(65) Prior Publication Data

US 2008/0225268 A1    Sep. 18, 2008

(51) Int. Cl.
    *G01N 23/00*    (2006.01)
(52) U.S. Cl. .............. 250/306; 250/307; 250/492.1; 250/440.11; 250/492.2; 257/414; 257/428; 257/431; 257/433; 356/300; 356/301; 977/700; 977/701; 977/720; 977/723
(58) Field of Classification Search .............. 250/306, 250/307, 492.1, 440.11, 492.2; 257/414, 257/428, 431, 433; 356/300, 301; 977/700, 977/701, 720, 723
    See application file for complete search history.

(56) References Cited

U.S. PATENT DOCUMENTS

2006/0034729 A1*  2/2006  Poponin ............... 422/82.05
2006/0038990 A1*  2/2006  Habib et al. ............. 356/301
2006/0164634 A1*  7/2006  Kamins et al. ........... 356/301
2008/0079104 A1*  4/2008  Stewart et al. ........... 257/433
2008/0198376 A1*  8/2008  Poponin ................ 356/301
2009/0002701 A1*  1/2009  Fattal et al. ............. 356/301
2009/0079978 A1*  3/2009  Kimura ................. 356/301

OTHER PUBLICATIONS

Meier, et al ("Enhanced fields on rough surfaces: dipolar interactions among particles of sizes exceeding the Rayleigh limit" Journal of the Optical Society of America B: Optical Physics 2(6) 1985 pp. 931-949.*

White, Ian M., et al., " Spectroscopy—Increasing the Enhancement of SERS with Dielectric Microsphere Resonators", Spectroscopy Mag., Apr. 1, 2006, pp. 1-5.

* cited by examiner

*Primary Examiner*—David A Vanore
*Assistant Examiner*—Michael Maskell

(57) ABSTRACT

In one aspect of the present invention, an electric-field-enhancement structure is disclosed. The electric-field-enhancement structure includes a substrate and an ordered arrangement of dielectric particles having at least two adjacent dielectric particles spaced from each other a controlled distance. The controlled distance is selected so that when a resonance mode is excited in each of the at least two adjacent dielectric particles responsive to excitation electromagnetic radiation, each of the resonance modes interacts with each other to result in an enhanced electric field between the at least two adjacent dielectric particles. Other aspects of the present invention are electric-field-enhancement apparatuses that utilize the described electric-field-enhancement structures, and methods of enhancing an electric field between adjacent dielectric particles.

18 Claims, 15 Drawing Sheets

ELECTRIC-FIELD-ENHANCEMENT STRUCTURES INCLUDING DIELECTRIC PARTICLES, APPARATUS INCLUDING SAME, AND METHODS OF USE

TECHNICAL FIELD

Embodiments of the present invention are related generally to electric-field-enhancement structures. More particularly, embodiments of the present invention relate to electric-field-enhancement structures including an ordered arrangement of dielectric particles for enhancing an incident electric field between adjacent dielectric particles.

BACKGROUND

Enhancement of electric fields around metal particles is a topic of current scientific and technological interest. For example, surface enhanced Raman spectroscopy ("SERS") is a well-known spectroscopy technique that utilizes an enhanced electric field near a specially prepared, roughened metal surface or metal particles to increase a Raman signal from an analyte. In SERS, the analyte is adsorbed onto, or placed adjacent to, an activated metal surface or structure. Irradiation of the analyte and the metal surface or particles with light of a selected frequency excites surface plasmons in the metal surface or particles. The surface plasmon frequency is relatively independent of surface or particle geometry and is predominately a function of the composition of the metal.

During SERS, the analyte experiences the intense, localized electric field of the surface plasmons, and Raman photons characteristic of the analyte are scattered from the analyte. The enhanced electric field is considered one significant factor for the relatively increased Raman signal compared to when Raman spectroscopy is practiced without the metal surface or particles. For example, the enhanced electric field from the metal surface may enhance the Raman scattering intensity by factors of between $10^3$ and $10^6$.

Recently, Raman spectroscopy has been performed employing randomly oriented metal nanoparticles, such as nanometer scale needles, islands, and wires, as opposed to a simple roughened metal surface, for enhancing electric fields. The intensity of the Raman scattered photons from a molecule adsorbed on such a metal surface may be increased by factors as high as $10^{16}$. At this level of sensitivity, Raman spectroscopy has been used to detect single molecules and is commonly referred to as nano-enhanced Raman spectroscopy ("NERS").

As can be appreciated from the discussion above about SERS and NERS, enhancement of electric fields around metal particles can be of significant utility. In addition to SERS and NERS, enhancement of electric fields can be used in other applications, such as sensors, Raman imaging systems, nanoantennas, and many other applications. Regardless of the particular application, electric field enhancement using metal particles or surfaces has several limitations. The frequency at which light can be coupled to either localized or surface plasmons is relatively independent of the surface or particle geometry and is predominately a function of the composition of the metal. Thus, altering the size or geometry of the metal surface or metal particles has only a minor effect on the frequency at which light can be coupled to the surface plasmons. Accordingly, the frequency at which light can be coupled to surface plasmons is essentially fixed by the composition of the metal surface or particles, which limits their usefulness in many applications.

In addition to lack of scalability, many types of metal nanoparticles are known to be toxic. Metal nanoparticle toxicity can make safe-manufacturing of electric-field-enhancement structures difficult, and may limit application of electric-field-enhancement structures including metal nanoparticles in certain biomedical applications. Furthermore, fabrication of electric-field-enhancement structures with metal particles typically relies on a self-assembled distribution of the metal nanoparticles. Thus, it can be difficult to precisely space or align metal nanoparticles.

Therefore, researchers and developers of electric-field-enhancement structures can appreciate a need for a scalable and less-toxic electric-field-enhancement structure for use in a wide variety of applications, such as sensors, Raman spectroscopy systems, and many other applications.

SUMMARY

Various aspects of the present invention are directed to electric-field-enhancement structures for enhancing an incident electric field between adjacent dielectric particles, electric-field-enhancement apparatuses, and methods of enhancing an electric field between adjacent dielectric particles. In one aspect of the present invention, an electric-field-enhancement structure is disclosed. The electric-field-enhancement structure includes a substrate and an ordered arrangement of dielectric particles having at least two adjacent dielectric particles spaced from each other a controlled distance. The controlled distance is selected so that when a resonance mode is excited in each of the at least two adjacent dielectric particles responsive to excitation electromagnetic radiation, each of the resonance modes interacts with each other to result in an enhanced electric field between the at least two adjacent dielectric particles.

In another aspect of the present invention, an electric-field-enhancement apparatus is disclosed. The electric-field-enhancement apparatus includes an excitation light source operable to output excitation electromagnetic radiation. The electric-field-enhancement apparatus further includes an electric-field-enhancement structure. The electric-field-enhancement structure includes an ordered arrangement of dielectric particles having at least two adjacent dielectric particles spaced from each other a controlled distance. The controlled distance is selected so that when a resonance mode is excited in each of the at least two adjacent dielectric particles responsive to the excitation electromagnetic radiation, each of the resonance modes interacts with each other to result in an enhanced electric field between the at least two adjacent dielectric particles.

In yet another aspect of the present invention, a method of enhancing an electric field between at least two adjacent dielectric particles is disclosed. The method includes irradiating the at least two adjacent dielectric particles with excitation electromagnetic radiation having a frequency selected to excite a resonance mode in each of the at least two adjacent dielectric particles. The method further includes positioning the at least two dielectric particles sufficiently close to each other so that each of the resonance modes interacts with each other to result in an enhanced electric field between the at least two adjacent dielectric particles.

BRIEF DESCRIPTION OF THE DRAWINGS

The drawings illustrate various embodiments of the present invention, wherein like reference numerals refer to like elements or features in different views or embodiments shown in the drawings.

DETAILED DESCRIPTION OF VARIOUS EMBODIMENTS

Figure 1:
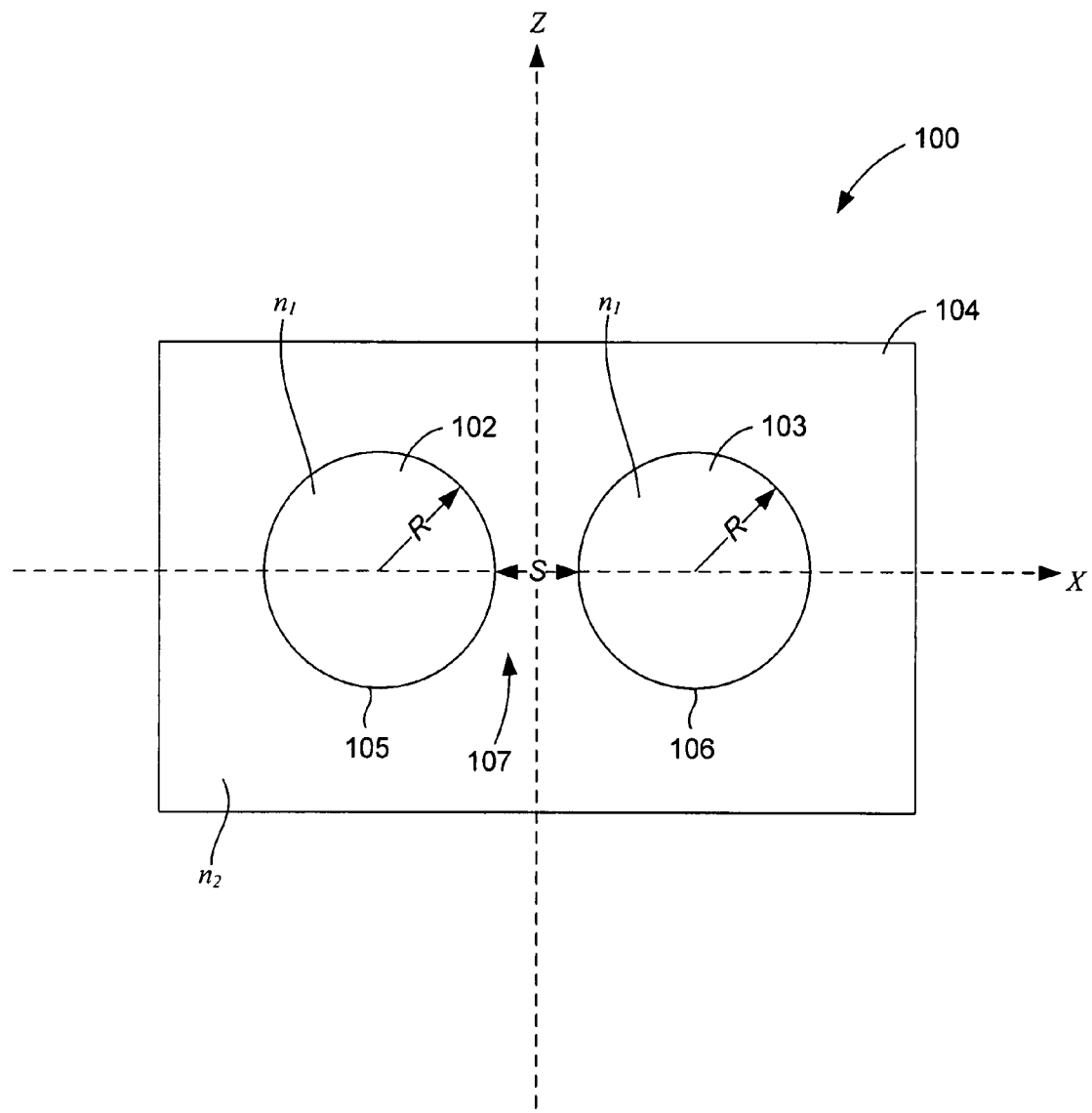
FIG. 1 is a schematic top plan view of an electric-field-enhancement structure according to one embodiment of the present invention.
Figure 2:
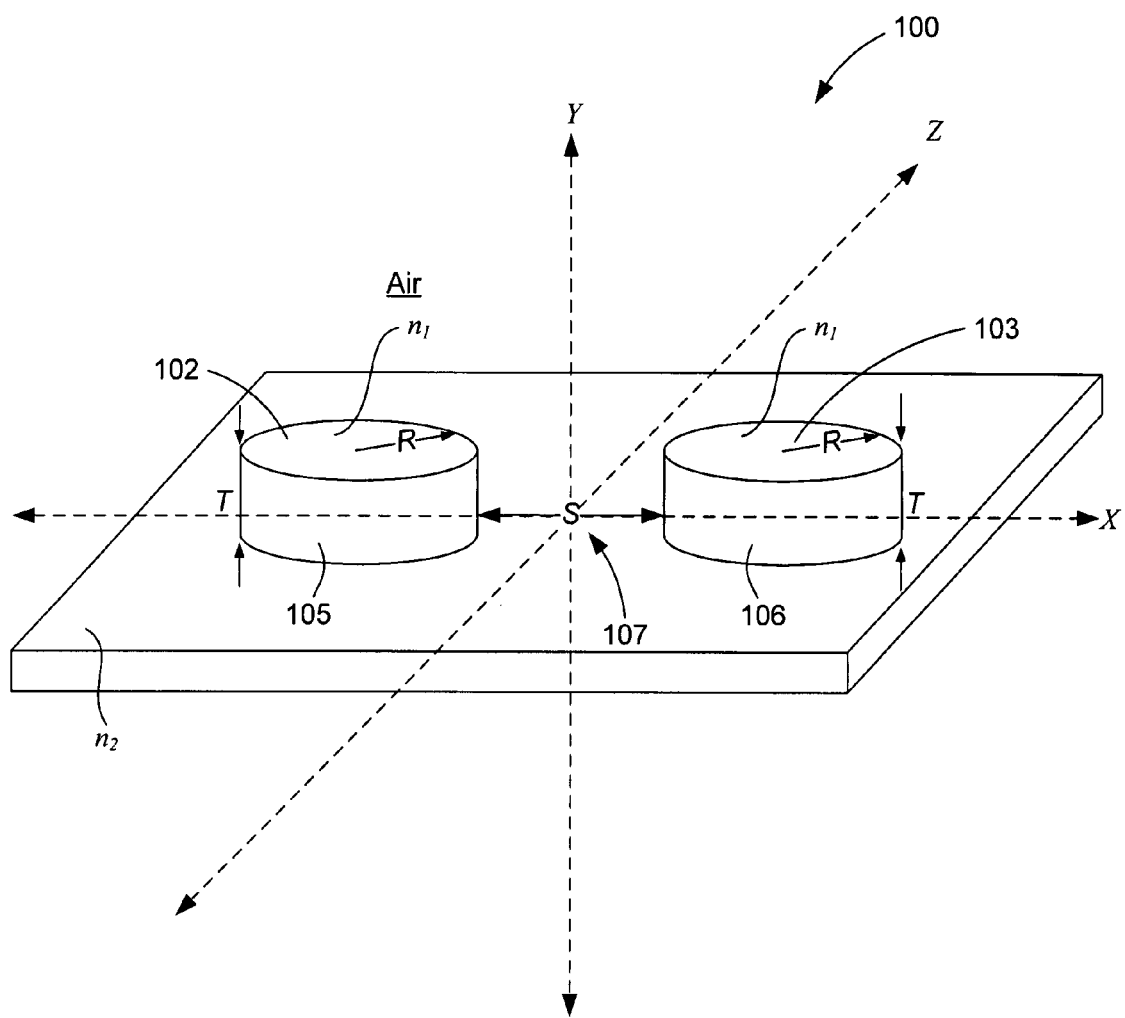
FIG. 2 is a schematic isometric view of the electric-field-enhancement structure shown in FIG. 1.

Various embodiments of the present invention are directed to electric-field-enhancement structures, electric-field-enhancement apparatuses, and methods of enhancing an electric field between adjacent dielectric particles. FIGS. 1 and 2 show an electric-field-enhancement structure 100 according to one embodiment of the present invention. The electric-field-enhancement structure 100 includes at least two adjacent dielectric particles 102 and 103 affixed to the substrate 104. Each of the dielectric particles 102 and 103 may be disk-shaped having a radius R, a thickness T, and corresponding peripheral surfaces 105 and 106. For example, the radius R and thickness T of each of the dielectric particles 102 and 103 may be about 50 nm to about 3000 nm and about 50 nm to about 300 nm, respectively. The dielectric particles 102 and 103 are distributed along an X axis and spaced from each other a controlled spacing S to define an intermediate enhancement region 107 therebetween. The intermediate enhancement region 107 is the gap between closest portions of the adjacent dielectric particles 102 and 103. The spacing S may range from, for example, greater than zero to about 50 nm.

The dielectric particles 102 and 103 may be made from a non-metallic material having a relatively high index of refraction, $n_1$, compared to the index of refraction of the surrounding medium. Thus, the index of refraction $n_1$ is greater than the index of refraction $n_2$ of the substrate 104 and surrounding air. For example, the dielectric particles 102 and 103 may be made from silicon (n=5.009 at 425 nm), germanium (n=5.9 at 605 nm), gallium arsenide (n=5.107 at 430 nm), another semiconductor material, titanium dioxide (n=5.38 at 318 nm), or another suitable relatively high-index material that can be processed using micro-fabrication or nano-fabrication techniques. The substrate 104 may be, for example, a glass substrate made from silica or another suitable relatively low-index material. The dielectric particles 102 and 103 may be formed on the substrate 104 using a number of different well-known micro-fabrication and nanofabrication techniques by, for example, depositing a dielectric layer using a physical or chemical deposition process on the substrate 104 followed by photolithographically defining the dielectric particles 102 and 103 from the deposited dielectric layer.

Figure 3:
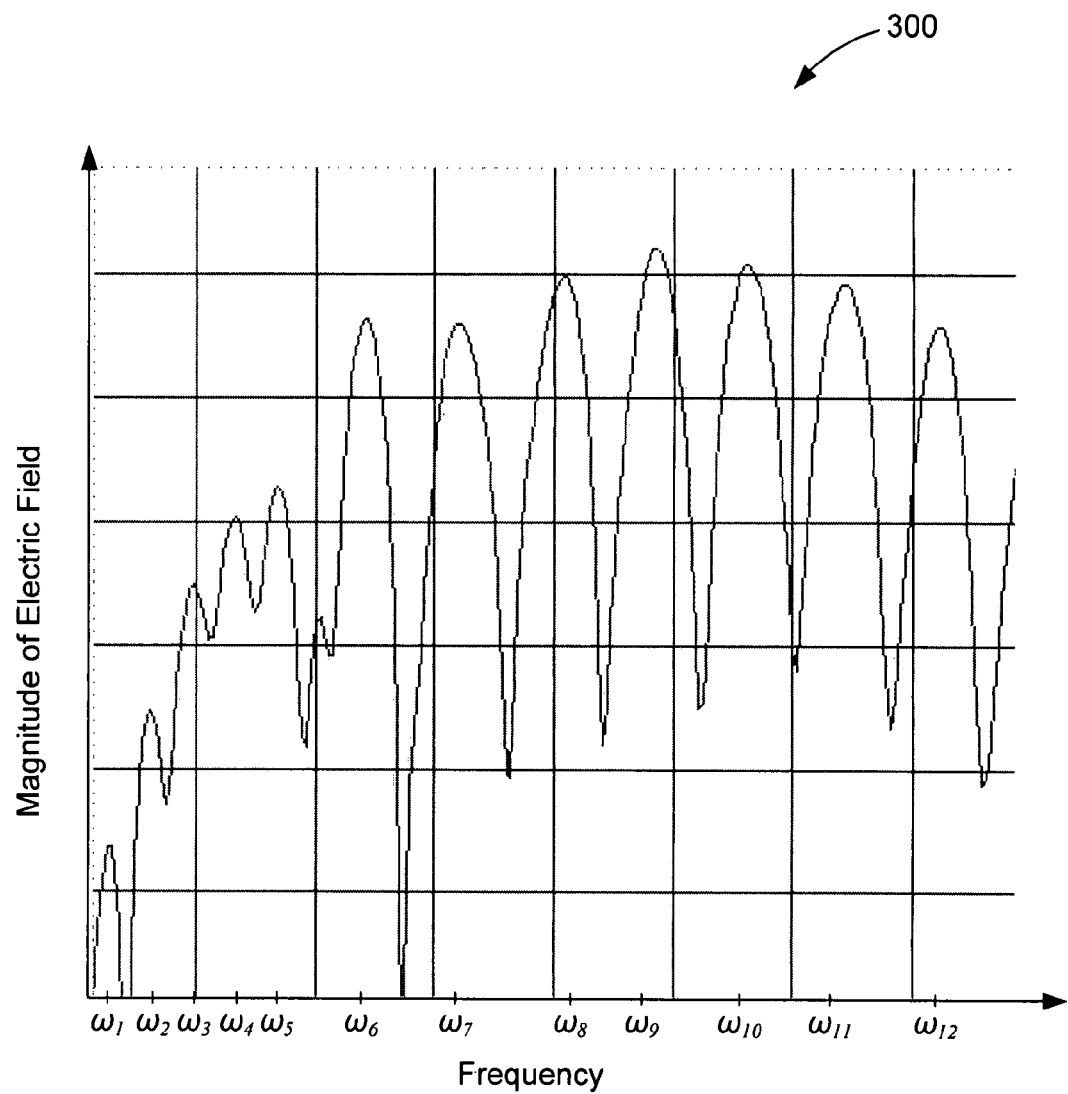
FIG. 3 is a graph illustrating a number of resonance modes that may be excited in each dielectric particle shown in FIGS. 1 and 2.

As best shown in FIG. 2, the dielectric particles 102 and 103 are surrounded by the low-index substrate 104 and the surrounding air. Accordingly, resonance modes may be excited in the dielectric particles 102 and 103 by proper selection of excitation electromagnetic radiation ("EMR") characteristics from a light source (not shown), such as electric field polarization direction and frequency. FIG. 3 is a graph 300 that illustrates a number of different resonance modes $\omega_1$-$\omega_{12}$ that are excitable in each of the dielectric particles 102 and 103 by irradiation of the dielectric particles 102 and 103 using excitation EMR having a properly selected frequency. For example, irradiating the dielectric particle 102 with excitation EMR having a frequency at or near $\omega_1$ couples the incident EMR to the lowest-order resonance mode of the dielectric particle 102. The resonance frequencies may be associated with one of X, Y, or Z electric field components. For example, the resonance frequencies $\omega_1$-$\omega_{12}$ shown in FIG. 3 can be frequencies at which an x-component of the electric field of the EMR excites resonance modes in each dielectric particle 102 and 103. Thus, incident EMR having, for example, an x-component of the electric field with a frequency $\omega_1$ can excite the lowest-order resonance mode in each of the dielectric particles 102 and 103. Other components of the electric field may excite resonance modes at the same or different frequencies depending upon the symmetry of the dielectric particles 102 and 103. For dielectric particles having the representative dimensions and indices of refraction discussed above, the resonant frequencies are typically in the terra hertz range.

It is noted that the graph 300 is merely for illustrative purposes, and the shape of the graph and frequency of the resonances is highly dependent of the geometry and index of refraction of the dielectric particles 102 and 103. Additionally, changing the size, shape, and/or index of refraction of a dielectric particle may significantly change the frequency spectrum of the resonance modes. The frequency spectrum of each dielectric particle 102 and 103 is scalable, and decreasing the particle size by a factor of, for example, ten will increase the frequency of the resonance modes by a corresponding factor of ten. Thus, the resonance frequencies may be controllably altered by changing size of the dielectric particles 102 and 103. Additionally, changing the difference in the index of refraction between the dielectric particles 102 and 103 and the substrate 104 and the surrounding medium also alters the frequency spectrum. The greater the difference between the index of refraction of the dielectric particles 102 and 103 and the surrounding medium (i.e., the substrate 104 and air), the smaller the size the dielectric particles 102 and 103 may be made while still supporting resonance modes.

Figure 4:
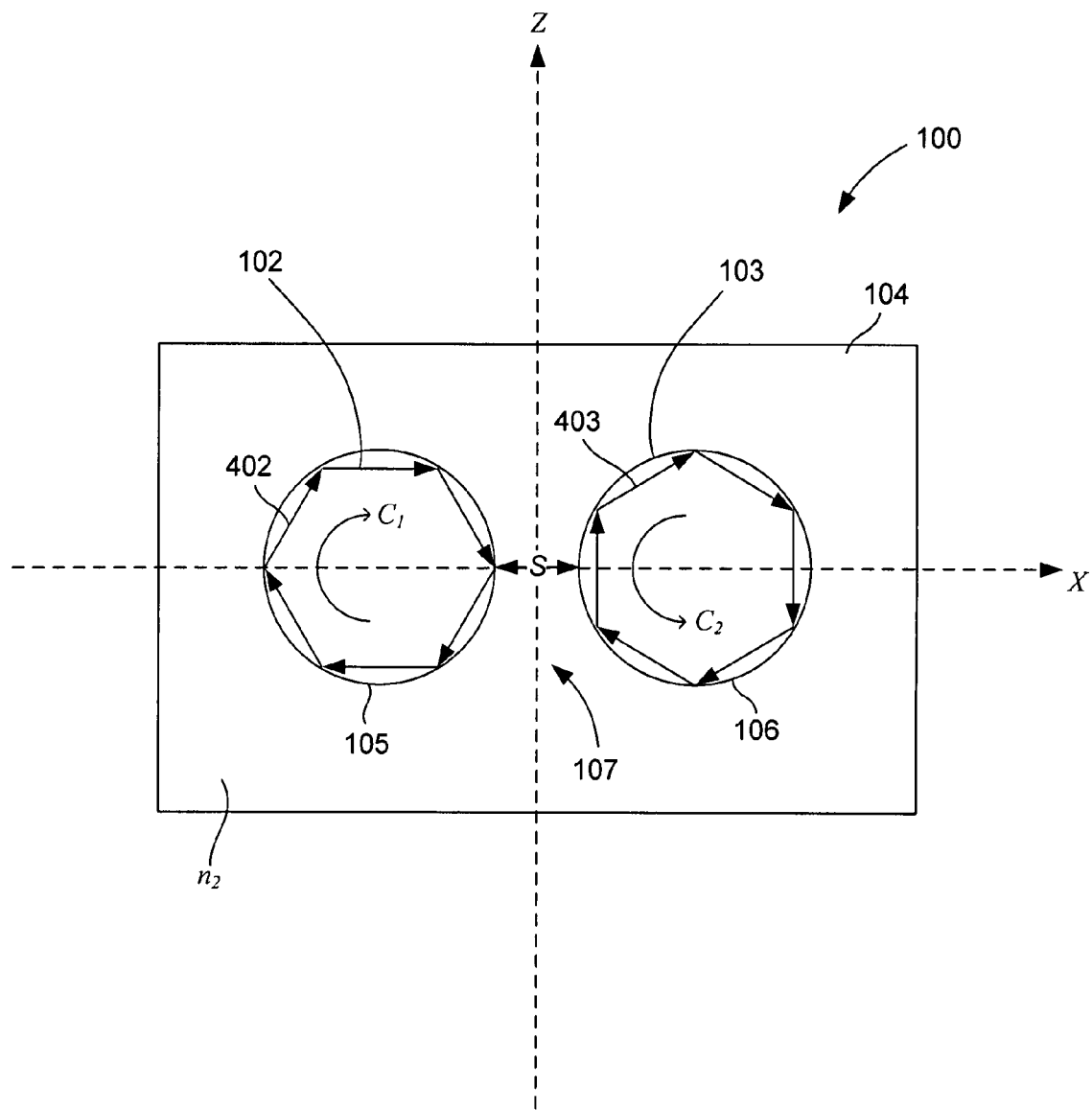
FIG. 4 is a schematic diagram illustrating whispering gallery modes confined and propagating within each dielectric particle shown in FIGS. 1 and 2.

The type of resonance modes that may be excited in each of the dielectric particles 102 and 103 are also known as whispering gallery modes. Whispering gallery modes occur at particular resonance frequencies for a dielectric particle of a given index of refraction and geometry. FIG. 4 schematically illustrates propagation of whispering gallery modes within each of the dielectric particles 102 and 103. As shown in FIG. 4, at one of the resonant frequencies, the EMR excites a mode of the dielectric particle 102 at the particular frequency and undergoes total internal reflection at the surface 105 of the dielectric particle 102 illustrated schematically as a light ray 402 that propagates circumferentially in a direction $C_1$. The EMR also excites a mode of the dielectric particle 103 and undergoes total internal refraction at the surface 106 of the dielectric particle 103 illustrated schematically as a light ray 403 that propagates circumferentially in a direction $C_2$. The EMR becomes trapped within the dielectric particles 102 and 103 for timescales which depend on the size of the particles and the Q factor of the modes. A quality factor ("Q-factors") that quantitatively describes the extent of the confinement of the incident EMR within respective dielectric particles 102 and 103 may be on the order of about $10^6$ to about $10^{10}$. The Q-factor is an indication of the number of times that the confined EMR propagates circumferentially within the dielectric particles 102 and 103. The confined EMR is concentrated near the surfaces 105 and 106 of the corresponding dielectric particles 102 and 103, and the intensity of the electric field of the EMR decays evanescently with distance radially outward from the peripheral surfaces 105 and 106 into the intermediate enhancement region 107.

By controlling the spacing S between the adjacent dielectric particles 102 and 103 and properly exciting one of the resonance modes of the dielectric particles 102 and 103, the individual resonance modes excited in each of the dielectric particles 102 and 103 interact to locally enhance the electric field of the excitation EMR in the intermediate enhancement region 107 between the dielectric particles 102 and 103. Although the precise physical phenomenon is not completely understood, the inventors currently believe that the individual evanescent electric fields associated with the resonance modes of each of the dielectric particles 102 and 103 couple with each other to locally enhance the electric field of the excitation EMR within the intermediate enhancement region 107. The enhancement of the electric field between the dielectric particles 102 and 103 may be between about 10 to about 300 times the electric field of the excitation EMR.

Figure 5:
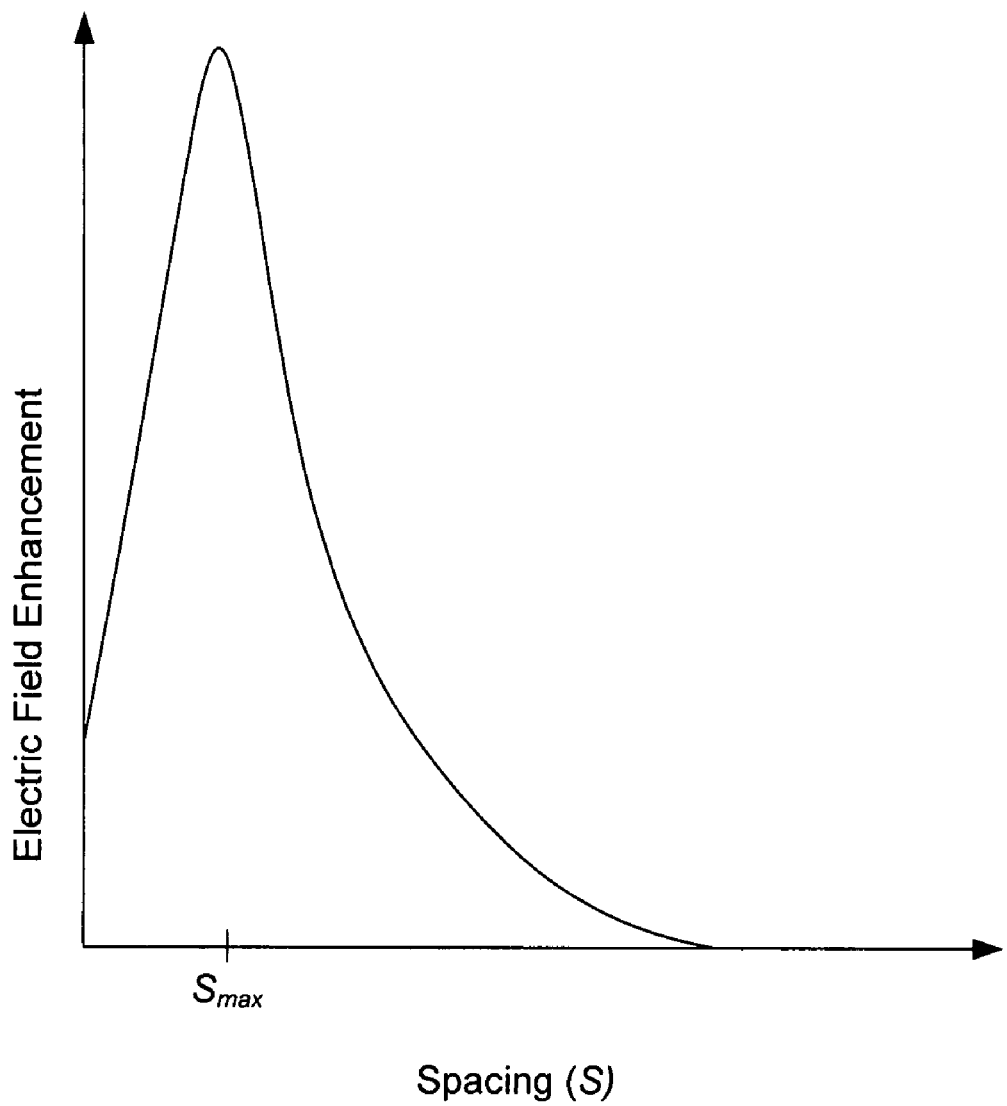
FIG. 5 is a graph showing electric field enhancement as a function of spacing between the adjacent dielectric particles shown in FIGS. 1 and 2.

The extent of enhancement of the electric field of the excitation EMR in the intermediate enhancement region 107 between the dielectric particle 102 and 103 is dependent on the spacing S. Electric field enhancement is defined as the ratio of the intensity of the maximum electric field generated within or proximate the intermediate enhancement region 107 to the intensity of the electric field of the excitation EMR. As shown in FIG. 5, at a spacing $S_{max}$, the enhancement of the electric field of the excitation EMR is at a maximum. The enhancement effect decreases when the spacing S of the adjacent dielectric particles 102 and 103 is less than $S_{max}$. When the spacing S of the adjacent dielectric particles 102 and 103 is greater than $S_{max}$, the enhancement effect also decreases. Accordingly, in one embodiment of the present invention, the spacing S is selected to be at or near $S_{max}$ in order to maximize enhancement of the electric field of the excitation EMR. The enhanced electric field is substantially constant for any location within the intermediate enhancement region 107 along an axis generally parallel to the Y axis.

Figure 6:
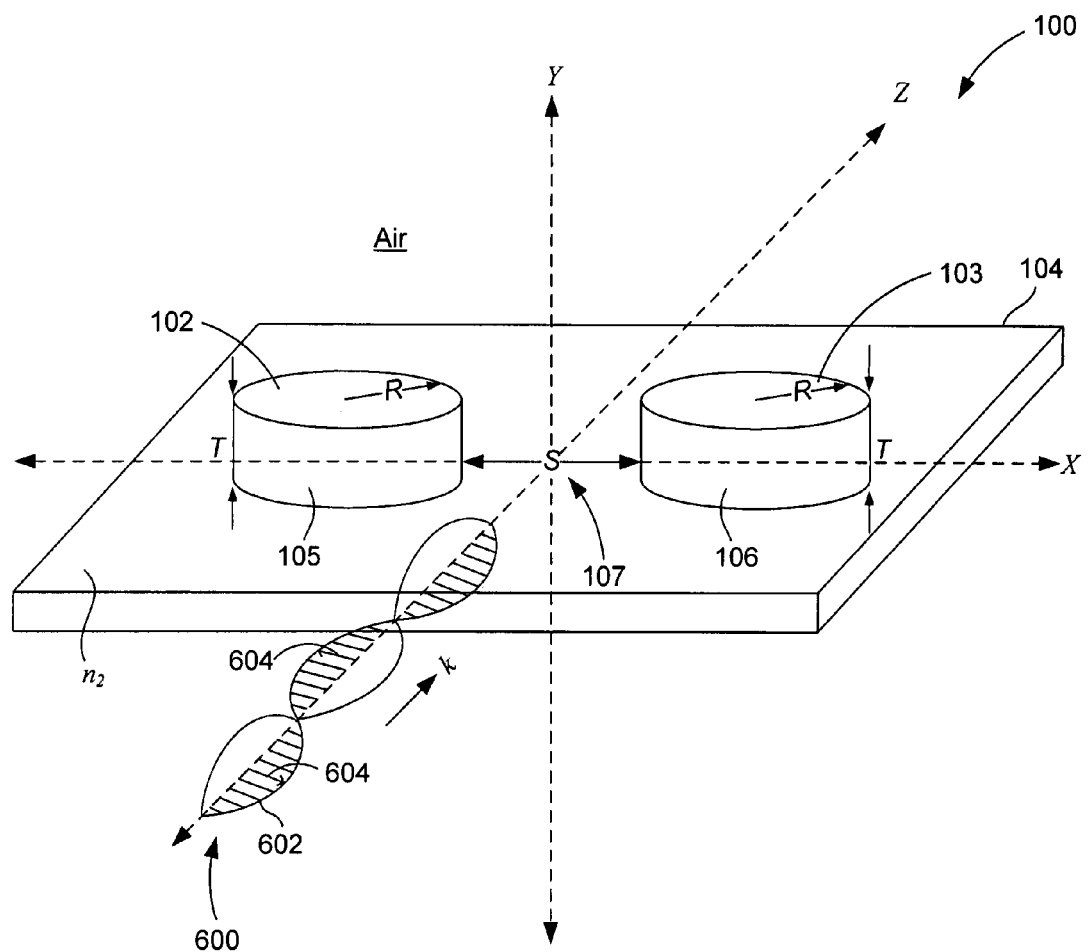
FIGS. 6 and 7 are schematic isometric views that illustrate different techniques for exciting resonance modes in the dielectric particles of the electric-field-enhancement structure shown in FIGS. 1 and 2 according to various embodiments of the present invention.
Figure 7:
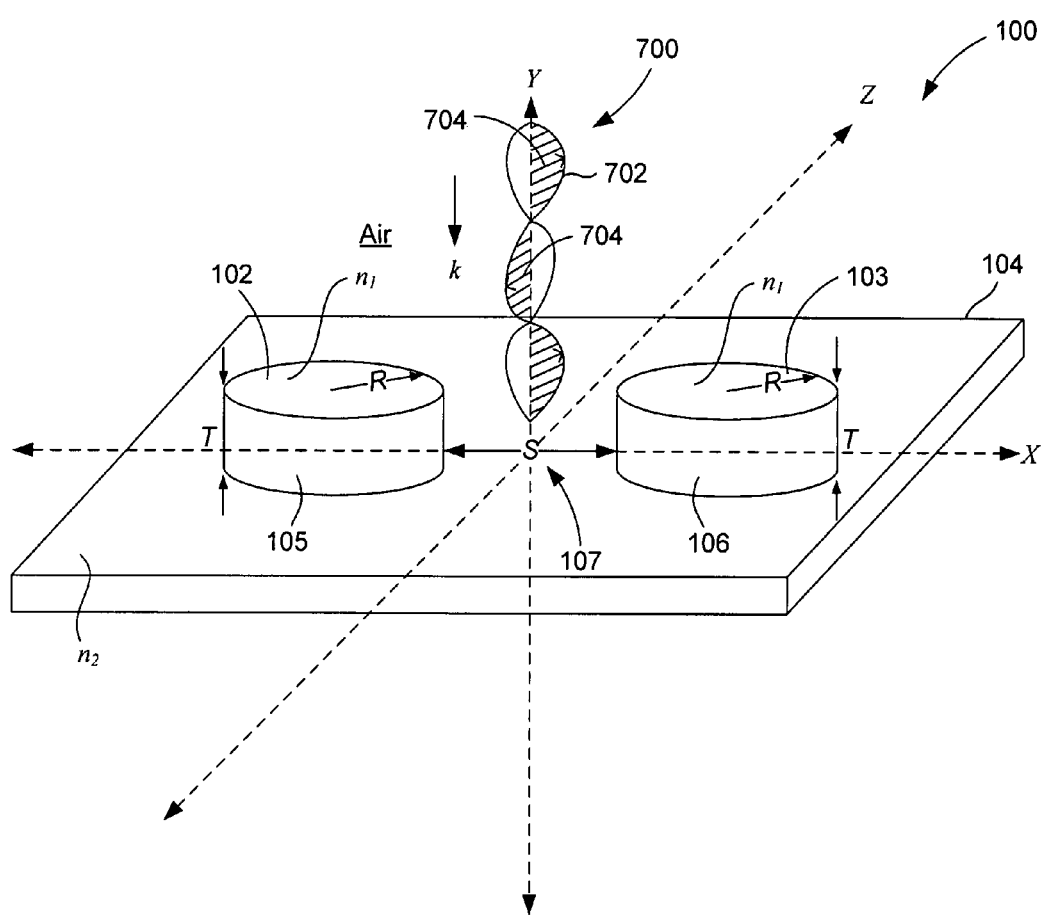

Although the electric field of the excitation EMR may be enhanced within the intermediate enhancement region 107 so long as excitation EMR is coupled to one of the resonance modes of each dielectric particle 102 and 103, the extent of enhancement of the electric field of the excitation EMR in the intermediate enhancement region 107 is dependent on the polarization direction of the electric field of the excitation EMR, and depending on the symmetry of the dielectric particles 102 and 103, the wavevector of the excitation EMR. FIGS. 6 and 7 illustrate different embodiments of the present invention for exciting the resonance modes within the dielectric particles 102 and 103. As shown in FIG. 6, in one embodiment of the present invention, excitation EMR 600 having an electric field 602 with a polarization direction 604 and a frequency at one of the resonance frequencies may irradiate the dielectric particles 102 and 103 in order to excite one of the resonance modes in each of the dielectric particles 102 and 103. As illustrated, the polarization direction 604 of the electric field 602 is generally parallel to the X axis along which the dielectric particles 102 and 103 are distributed and a wavevector k is generally parallel to the Z axis. In another embodiment of the present invention shown in FIG. 7, excitation EMR 700 having an electric field 702 with a polarization direction 704 and a frequency at one of the resonance frequencies may irradiate the dielectric particles 102 and 103 to excite one of the resonance modes in each of the dielectric particles 102 and 103. As illustrated in FIG. 7, the polarization direction 704 of the electric field 702 is generally parallel to the X axis and a wavevector k is generally parallel to the Y axis.

When the electric field of the excitation EMR is plane polarized in a direction generally parallel to the X axis, for the disk-shaped dielectric particles 102 and 103, a greater electric field enhancement for a given spacing S (FIG. 5) occurs when the wavevector k of the incident EMR is generally parallel to Z axis. This is due to the difference in the shape of the dielectric particles 102 and 103 along the Y and Z axes. When each of the dielectric particles 102 and 103 are shaped to exhibit spherical symmetry or cylindrical symmetry about the X axis, the electric field enhancement is the same for incident EMR with a wavevector k incident along a direction generally parallel to the Y or Z axes. Additionally, for incident electromagnetic radiation with the same wavevector k direction, electric field enhancement in the intermediate enhancement region 107 is greater when the polarization direction of the electric field of the excitation EMR is generally parallel to the X axis along which the dielectric particles 102 and 103 are distributed.

Figure 8:
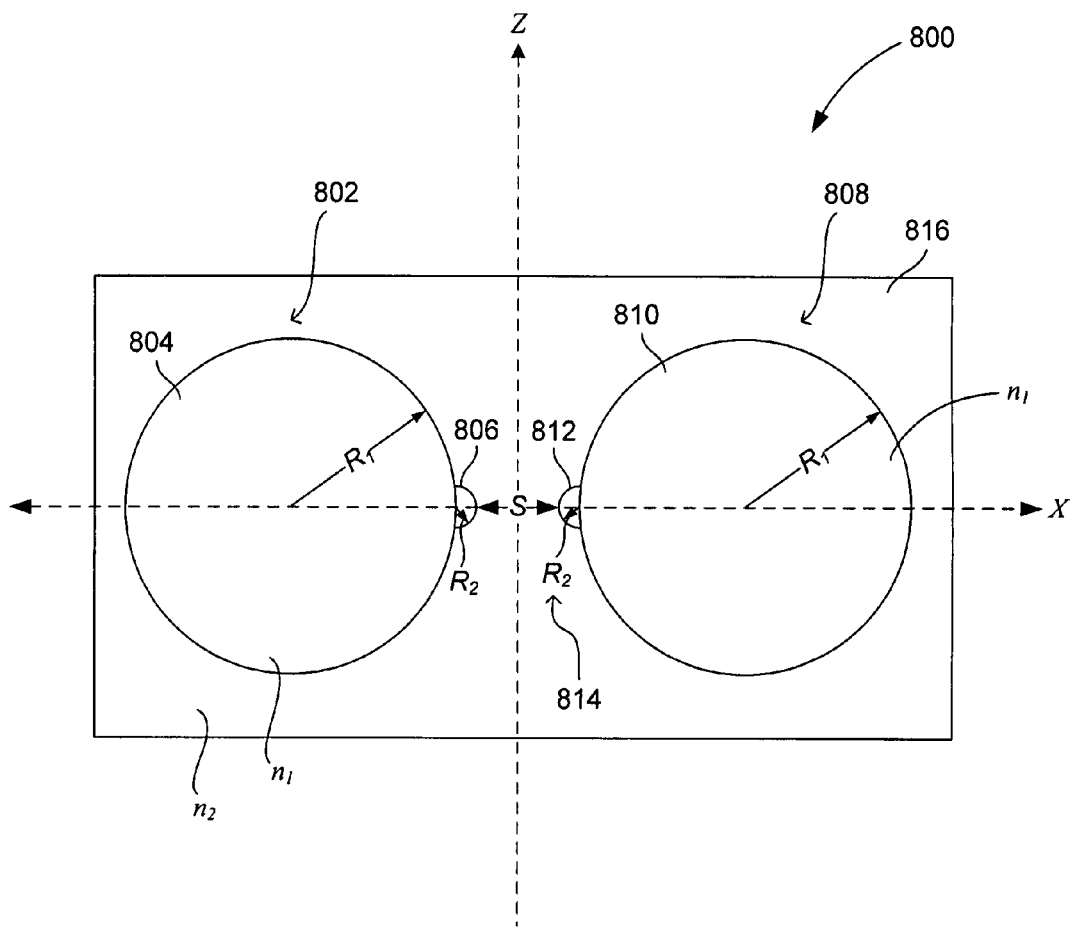
FIG. 8 is a schematic top plan view of an electric-field-enhancement structure according to another embodiment of the present invention.

In certain embodiments of the present invention, enhancement of electric field of the incident electromagnetic radiation may be further enhanced by controlling the dielectric particle geometry. FIG. 8 shows an electric-field-enhancement structure 800 according to one embodiment of the present invention. The electric-field-enhancement structure 800 includes a dielectric particle 802 having a first portion 804 with a radius $R_1$ and a second portion 806 projecting from the first portion 804 with a radius $R_2$ less than the radius $R_1$. The electric-field-enhancement structure 800 further includes a dielectric particle 808 having a first portion 810 with a radius $R_1$ and a second portion 812 projecting from the first portion 810 with a radius $R_2$ less than the radius $R_1$. $R_1$ may be, for example, about 100 to about 200 times the magnitude of $R_2$. For example, the radius $R_1$ and radius $R_2$ of each of the dielectric particles 802 and 808 may be about 500 nm to about 3000 nm and about 50 nm to about 30 nm, respectively. The dielectric particles 802 and 808 are oriented with the second portion 806 and the second portion 812 opposing each other, and the dielectric particles 802 and 808 are distributed along an X axis and spaced from each other a controlled spacing S to define an intermediate enhancement region 814 therebetween. The dielectric particles 802 and 808 are affixed to a substrate 816. The dielectric particles 802 and 808, and the substrate 816 may be made from the same materials and methods previously described with respect to the electric-field-enhancement structure 100 shown in FIGS. 1 and 2.

As can be appreciated from the relatively smaller radius $R_2$ compared to the radius $R_1$, the intensity of a resonance mode excited in each of the dielectric particles 802 and 808 is greater in the relatively smaller second portions 806 and 812. Accordingly, for the same spacing S and when the radius R of each of the dielectric particles 102 and 103 shown in FIG. 1 is equal to the radius $R_1$ of the dielectric particles 802 and 808 shown in FIG. 8, a relatively more enhanced electric field may be generated in the intermediate enhancement region 814 of the electric-field-enhancement structure 800 using any of the previously described excitation techniques.

The configurations for the dielectric particles shown in the electric-field-enhancement structures 100 and 800 merely represent some different embodiments of the present invention. In other embodiments of the present invention, the shape of the dielectric particles may be triangular, rectangular, or spherical. For example, instead of forming the dielectric particles using a micro-fabrication or a nano-fabrication process, such as conventional deposition and etching processes, generally spherical dielectric particles may distributed on a substrate to form an ordered array with a generally controlled spacing between the dielectric particles. Additionally, the shape and size of adjacent dielectric particles (e.g., dielectric particles 102 and 103 or dielectric particles 802 and 808) may be different provided that a resonance mode can be excited in each of the dielectric particles. For example, the same frequency excitation EMR may excite a lower-order resonance mode in one of the dielectric particles and a higher-order resonance mode in the other dielectric particle.

Figure 9:
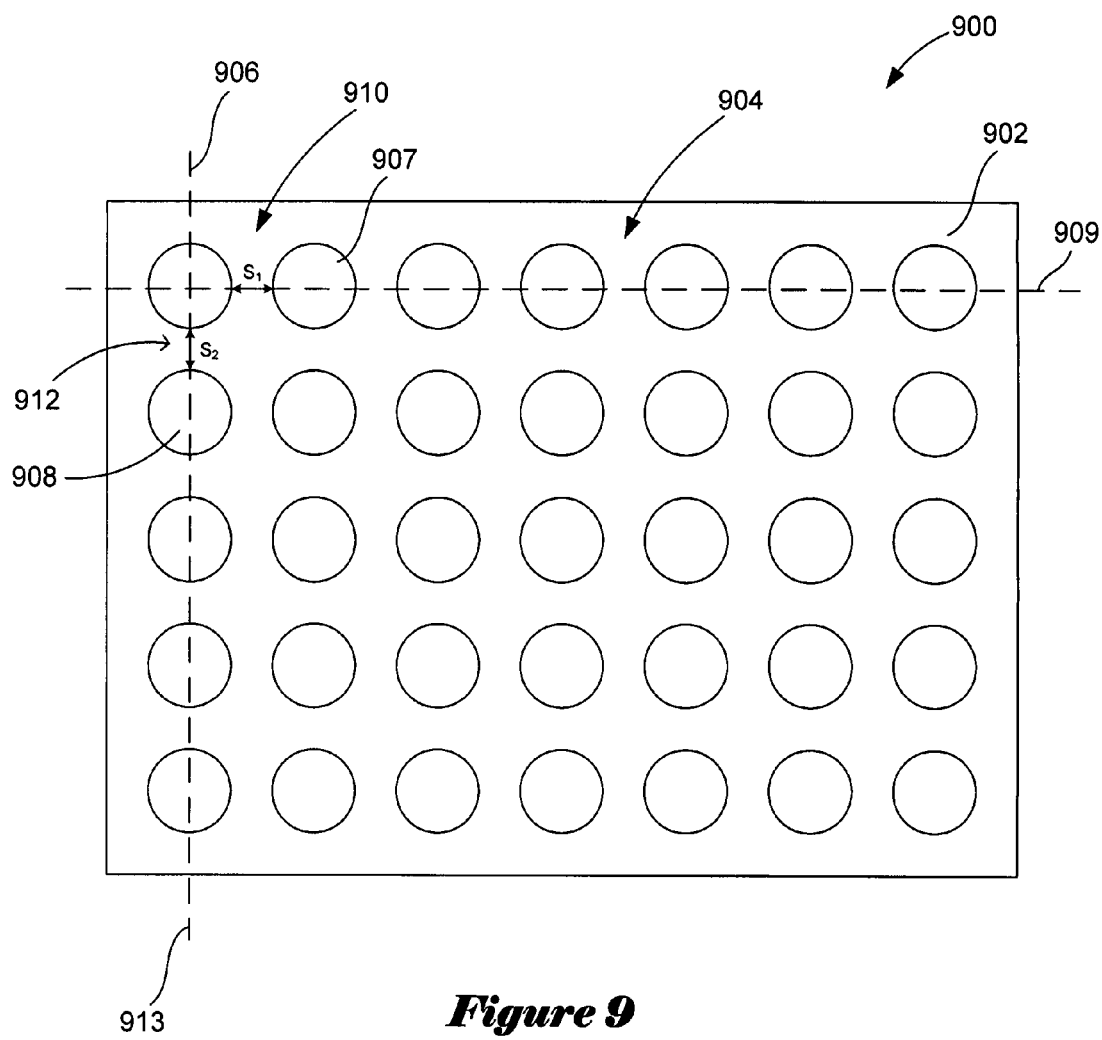
FIG. 9 is a schematic top plan view of an electric-field-enhancement structure including a two-dimensional, ordered array of dielectric particles according to yet another embodiment of the present invention.

Although the electric-field-enhancement structures 100 and 800 are illustrated with two adjacent dielectric particles, additional embodiments of the present invention are directed to an ordered two-dimensional array of dielectric particles in which the dielectric particles may be sized, spaced, and structured as in any of the previously described embodiments. FIG. 9 shows an electric-field-enhancement structure 900 according to another embodiment of the present invention. The electric-field-enhancement structure 900 includes a low-index substrate 902 having a two-dimensional ordered array 904 comprised of dielectric particles. For example, a dielectric particle 906 is spaced a controlled spacing $S_1$ from a dielectric particle 907, and the dielectric particle 906 is spaced a controlled spacing $S_2$ from a dielectric particle 908. The spacing $S_1$ and $S_2$ may be equal to each other or the spacing $S_1$ and $S_2$ may be different. In some embodiments of the present invention, each of the dielectric particles of the two-dimensional ordered array 904 may be configured with two or more projections that oppose corresponding projections of adjacent dielectric particles similar to the electric-field-enhancement structure 800 shown in FIG. 8.

As previously described, excitation electromagnetic radiation may irradiate the array 904 and the electric field may be enhanced within or proximate the intermediate enhancement regions 910 and 912 between adjacent dielectric particles. For example, the electric field polarization direction of the excitation electromagnetic radiation may be generally parallel to direction 909 or direction 913 and the wavevector of the excitation electromagnetic radiation may be generally perpendicular to the electric field polarization direction.

Figure 10:
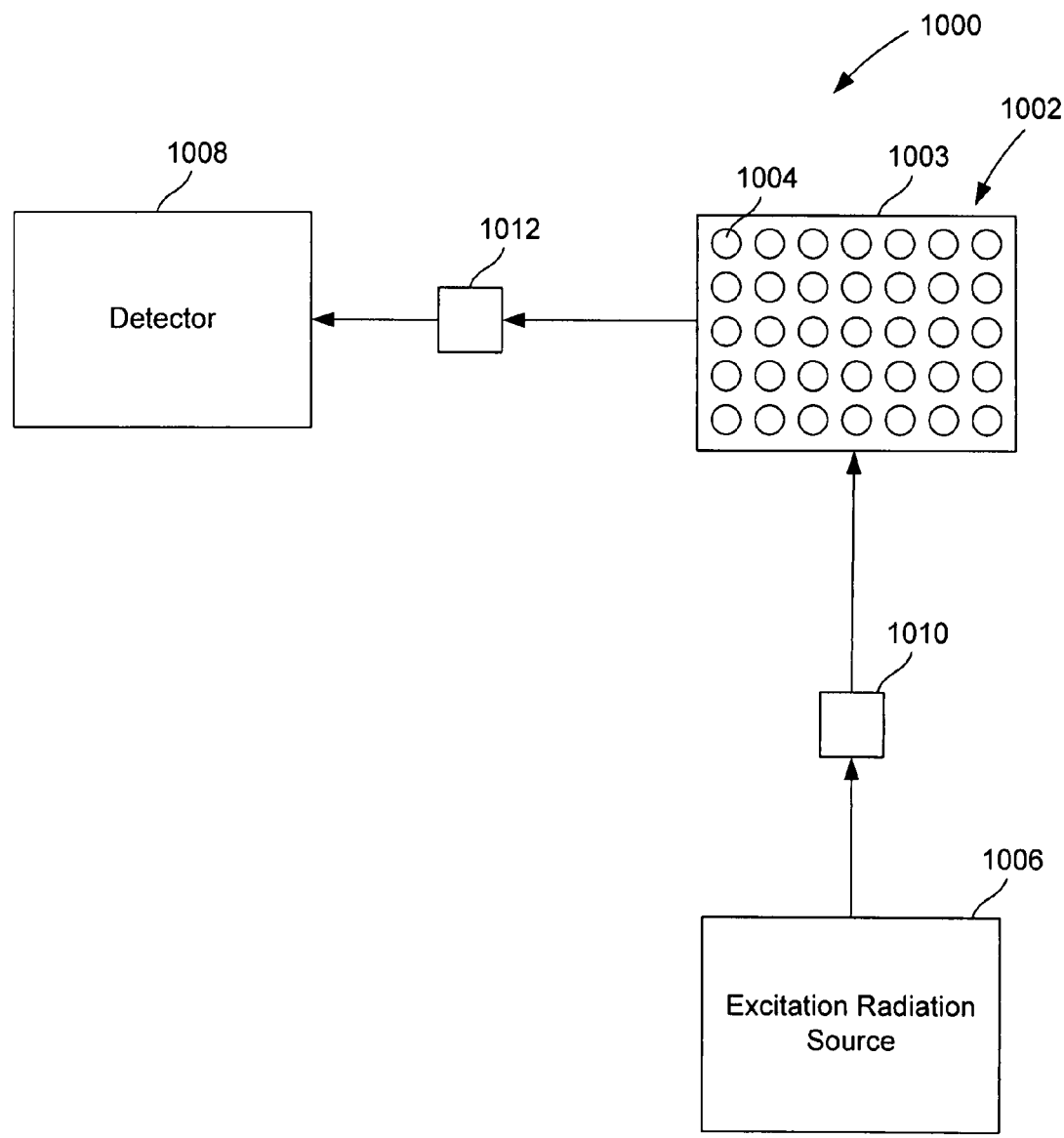
FIG. 10 is a functional block diagram of a Raman spectroscopy system that may use any of the disclosed electric-field-enhancement structures according to one embodiment of the present invention.

Any of the aforementioned embodiments of electric-field-enhancement structures shown and described with respect to FIGS. 1 through 9 may be used in a number of different electric-field-enhancement apparatuses. For example, FIG. 10 shows a functional block diagram of a Raman spectroscopy system 1000 according to one embodiment of the present invention. The Raman spectroscopy system 1000 includes an electric-field-enhancement structure 1002 having a substrate 1003 supporting a number of regularly-spaced dielectric particles 1004 structured to enhance an incident electric field, as previously described. For example, the electric-field-enhancement structure 1002 shown in FIG. 10 is configured as the electric-field-enhancement structure 900 shown in FIG. 9. The Raman spectroscopy system 1000 further includes an excitation EMR source 1006 and a detector 1008. The Raman spectroscopy system 1000 may also include various optical components 1010 positioned between the excitation EMR source 1006 and the electric-field-enhancement structure 1002, and various optical components 1012 positioned between the electric-field-enhancement structure 1002 and the detector 1008.

The excitation EMR source 1006 may include any suitable source for emitting EMR at a desired wavelength, and may be capable of emitting a tunable wavelength of radiation. For example, commercially available semiconductor lasers, helium-neon lasers, carbon dioxide lasers, light emitting diodes, incandescent lamps, and many other known radiation-emitting sources may be used as the excitation EMR source 1006. The EMR emitted by the excitation EMR source 1006 may be any suitable wavelength for analyzing an analyte using Raman spectroscopy and exciting at least one resonance mode of the dielectric particles 1004 of the electric-field-enhancement structure 1000. For example, the excitation EMR source 1006 may emit EMR having a range of wavelengths from about 350 nm to about 1000 nm. The excitation EMR emitted by the excitation EMR source 1006 may be delivered directly from the source 1006 to the electric-field-enhancement structure 1002. Alternatively, collimation, filtration, and subsequent focusing of the excitation radiation may be performed by optical components 1010 before the excitation EMR impinges on the electric-field-enhancement structure 1002. The optical components 1010 may further include one or more polarizing plates for selectively controlling a polarization direction of the excitation EMR.

The electric-field-enhancement structure 1002 may enhance the Raman signal of the analyte. In other words, irradiation of the dielectric particles 1004 of the electric-field-enhancement structure 1002 by excitation EMR from the excitation EMR source 1006 generates an enhanced electric field between adjacent dielectric particles 1004, as previously described, that may increase the number photons inelastically scattered by an analyte molecule positioned near or adjacent to the dielectric particles 1004.

The Raman scattered photons may be collimated, filtered, or focused with optical components 1012. For example, a filter or a plurality of filters may be employed, either as part of the structure of the detector 1008, or as a separate unit that is configured to filter the wavelength of the excitation radiation, thus allowing only the Raman scattered photons to be received by the detector 1008. The detector 1008 receives and detects the Raman scattered photons and may include a monochromator (or any other suitable device for determining the wavelength of the Raman scattered photons) and a device such as, for example, a photomultiplier for determining the quantity of Raman scattered photons (intensity). Ideally, the Raman scattered photons are scattered isotropically, being scattered in all directions relative to the electric-field-enhancement structure 1002. Thus, the position of the detector 1002 relative to the electric-field-enhancement structure 1002 is not particularly important. However, the detector 1008 may be positioned at, for example, an angle of ninety degrees relative to the direction of the incident excitation radiation to minimize the intensity of the incident excitation radiation that may be incident on the detector 1008.

To perform Raman spectroscopy using the Raman spectroscopy system 1000, a user may provide an analyte molecule or molecules adjacent to the dielectric particles 1004 of the electric-field-enhancement structure 1002. The analyte and the electric-field-enhancement structure 1002 are irradiated with excitation EMR from the excitation EMR source 1006. Then, Raman scattered photons scattered by the analyte are detected by the detector 1008.

Raman spectroscopy is merely one application in which the disclosed electric-field-enhancement structures may be used. Other applications include particle detectors or other sensing applications. In certain embodiments of the present invention, the Raman spectroscopy system 1000 may be re-configured to detect particles situated on the electric-field-enhancement structure 1002 by detecting, using the detector 908, shifting of the resonance modes for the dielectric particles 1004 as a result of a particle contacting one or more of the dielectric particles 1004. For example, by detecting the shift in the resonance modes from either the transmission or reflectance spectrum of the electric-field-enhancement structure 1002, the presence of one or more particles situated on the dielectric particles 1004 may be detected.

The following examples 1 through 5 of the present invention set forth various electric-field-enhancement structures including two adjacent dielectric particles and their calculated electric field intensities. Examples 1 through 5 provide further detail in connection with the various embodiments of the present invention described above. In examples 1 through 5, the electric field intensities were calculated using the well-known finite difference time domain ("FDTD") method. The intensity-contour plots of FIGS. 11 through 15 are shown in gray scale, with the maximum electric field intensity is normalized to zero decibels. The log of the absolute value of the electric field is shown in FIGS. 11 through 15, with lighter regions indicating a more intense calculated electric field. The silicon disks are shown slightly distorted from their true circular shape because the space grid used in the calculations for the region between the adjacent silicon particles is significantly finer than the space grid used for the other regions.

EXAMPLE 1

Figure 11:
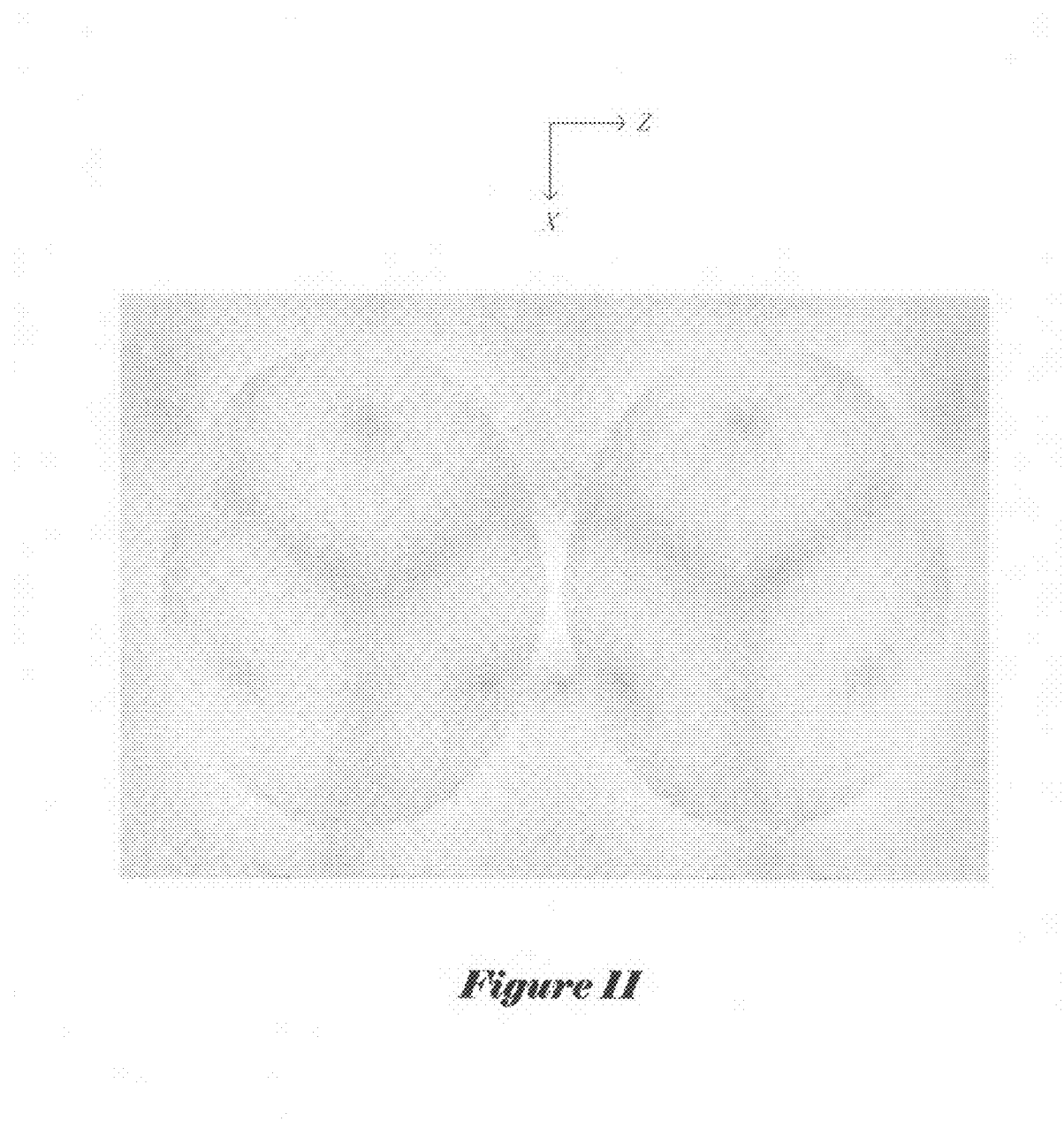
FIGS. 11 through 15 shows gray scale intensity-contour plots of the calculated electric field intensity for electric-field-enhancement structures according to examples 1 through 5 of the present invention, respectively.

FIG. 11 shows two adjacent silicon disks, each of which has a diameter of 2000 nm and a thickness of 200 nm. The spacing between the two adjacent silicon disks is 10 nm. The silicon disks are surrounded by air having a lower index of refraction than that of the silicon disks. The silicon disks are irradiated with excitation EMR having a frequency of 122.9 THz, which is at or near a resonance frequency of each of the silicon disks. The wavevector of the excitation EMR is generally parallel to the Z axis shown in FIG. 11. The polarization direction of the electric field of the excitation EMR is generally parallel to the X axis shown in FIG. 11. The calculated intensity of the resonance modes confined within each of the silicon disks and the calculated intensity of the electric field between the adjacent silicon disks is shown in FIG. 11. As calculated, the maximum electric field intensity is located between the silicon disks and is about 58.6 times greater than an intensity of the electric field of the excitation EMR.

EXAMPLE 2

Figure 12:
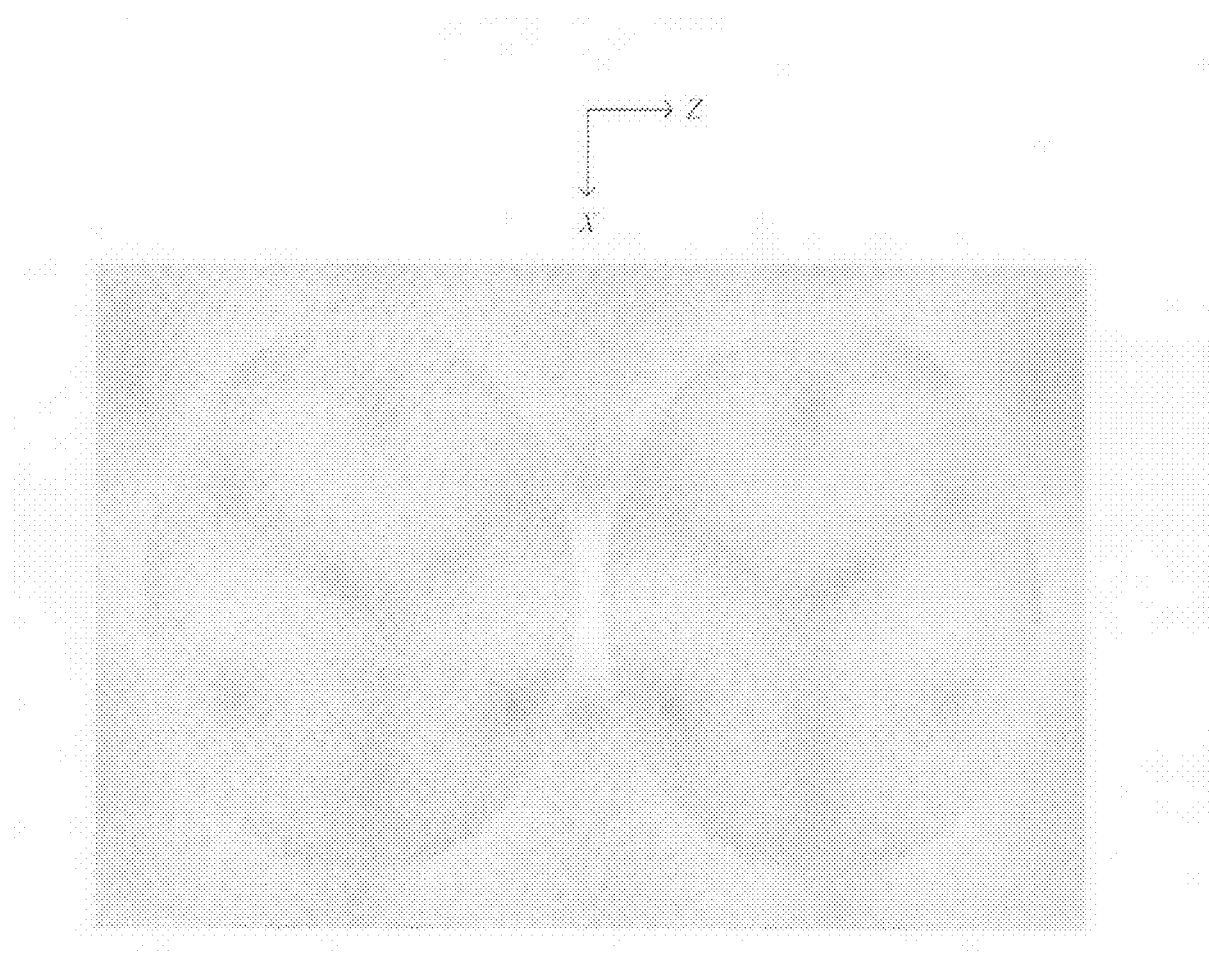

FIG. 12 shows two adjacent silicon disks, each of which has a diameter of 2000 nm and a thickness of 200 nm. The spacing between the two adjacent silicon disks is 20 nm. The silicon disks are surrounded by air having a lower index of refraction than that of the silicon disks. The silicon disks are irradiated with excitation EMR having a frequency of 123.6 THz, which is at or near a resonance frequency of each of the silicon disks. The wavevector of the excitation EMR is generally parallel to the Z axis shown in FIG. 12. The polarization direction of the electric field of the excitation EMR is generally parallel to the X axis shown in FIG. 12. The calculated intensity of the resonance modes confined within each of the silicon disks and the calculated intensity of the electric field between the adjacent silicon disks is shown in FIG. 12. As calculated, the maximum electric field intensity is located between the silicon disks and is about 46.8 times greater than an intensity of the electric field of the excitation EMR.

EXAMPLE 3

Figure 13:
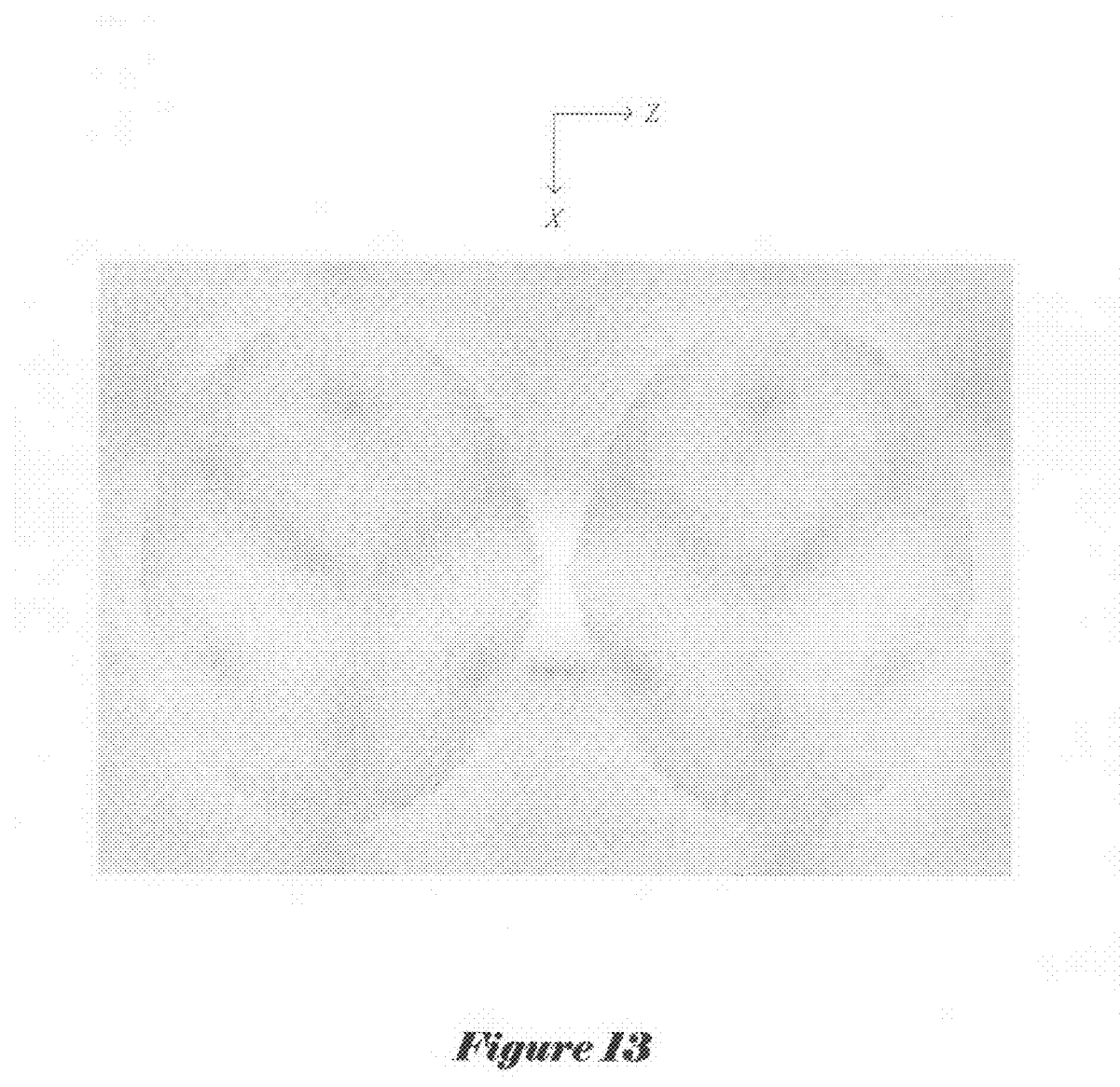

FIG. 13 shows two adjacent silicon disks, each of which has a diameter of 2000 nm and a thickness of 200 nm. The spacing between the two adjacent silicon disks is 5 nm. The silicon disks are surrounded by air having a lower index of refraction than that of the silicon disks. The silicon disks are irradiated with excitation EMR having a frequency of 121.852 THz, which is at or near a resonance frequency of each of the silicon disks. The wavevector of the excitation EMR is generally parallel to the Z axis shown in FIG. 13. The polarization direction of the electric field of the excitation EMR is generally parallel to the X axis shown in FIG. 13. The calculated intensity of the resonance modes confined within each of the silicon disks and the calculated intensity of the electric field between the adjacent silicon disks is shown in FIG. 13. As calculated, the maximum electric field intensity is located between the silicon disks and is about 81.8 times greater than an intensity of the electric field of the excitation EMR.

EXAMPLE 4

Figure 14:
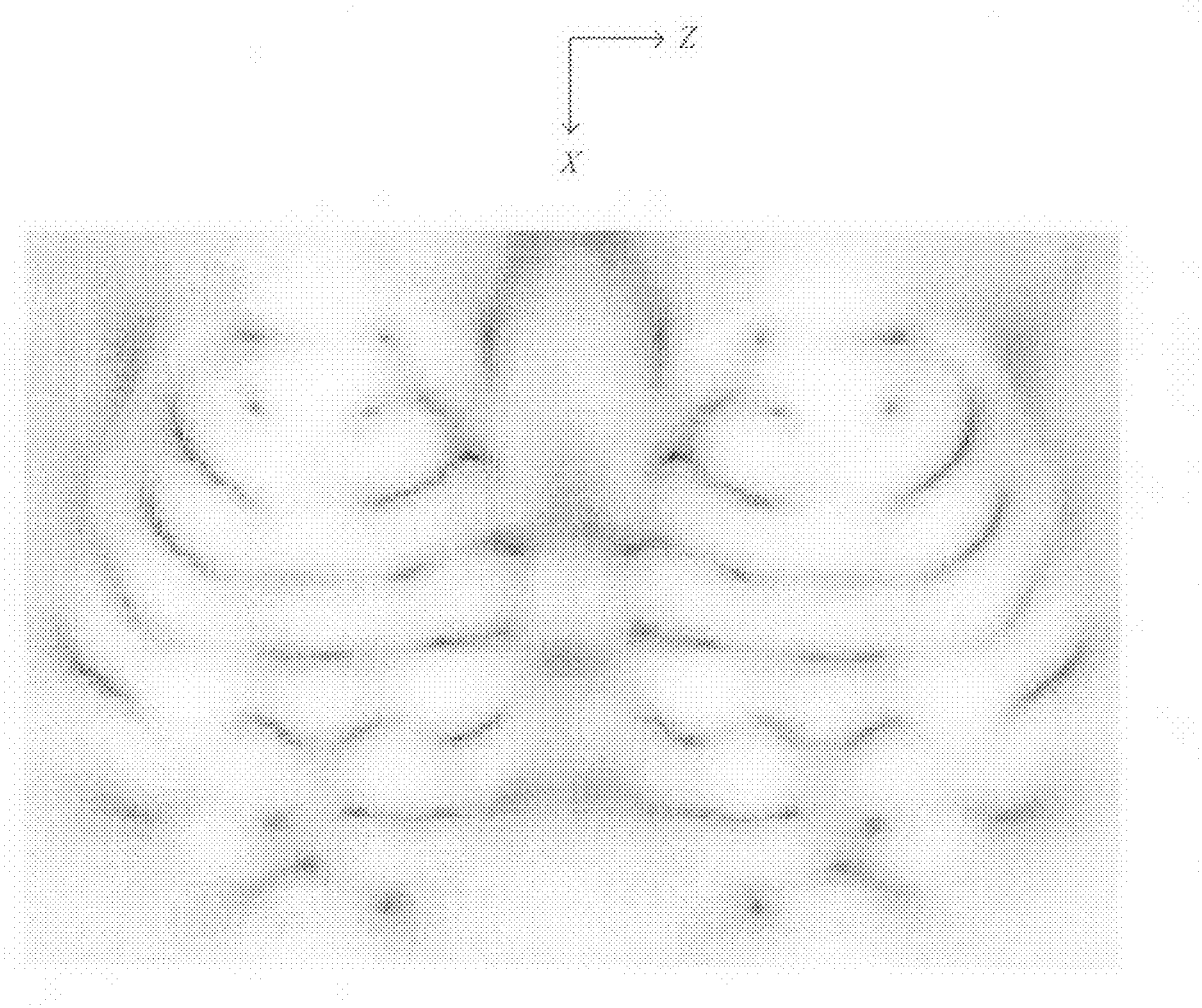

FIG. 14 shows two adjacent silicon disks, each of which has a diameter of 2000 nm and a thickness of 200 nm. The spacing between the two adjacent silicon disks is 20 nm. The silicon disks are surrounded by air having a lower index of refraction than that of the silicon disks. The silicon disks are irradiated with excitation EMR having a frequency of 123.6 THz, which is at or near a resonance frequency of each of the silicon disks. The wavevector of the excitation EMR is generally parallel to the Y axis that is perpendicular to the X and Z axes shown in FIG. 14. The polarization direction of the electric field of the excitation EMR is generally parallel to the X axis shown in FIG. 12. The calculated intensity of the resonance modes confined within each of the silicon disks and the calculated intensity of the electric field between the adjacent silicon disks is shown in FIG. 14. As calculated, the maximum electric field intensity located between the silicon disks and is about 18 times greater than an intensity of the electric field of the excitation EMR. Thus, examples 2 and 4 illustrate how the propagation direction of the excitation EMR can influence the electric field enhancement between the silicon disks. The electric field enhancement within the region between the silicon disks is about 2.6 times less when the wavevector of the excitation EMR is generally parallel to the Y axis as opposed to when the wavevector is generally parallel to the Z axis when the electric field polarization direction and disk composition, geometry, and spacing are the same.

EXAMPLE 5

Figure 15:
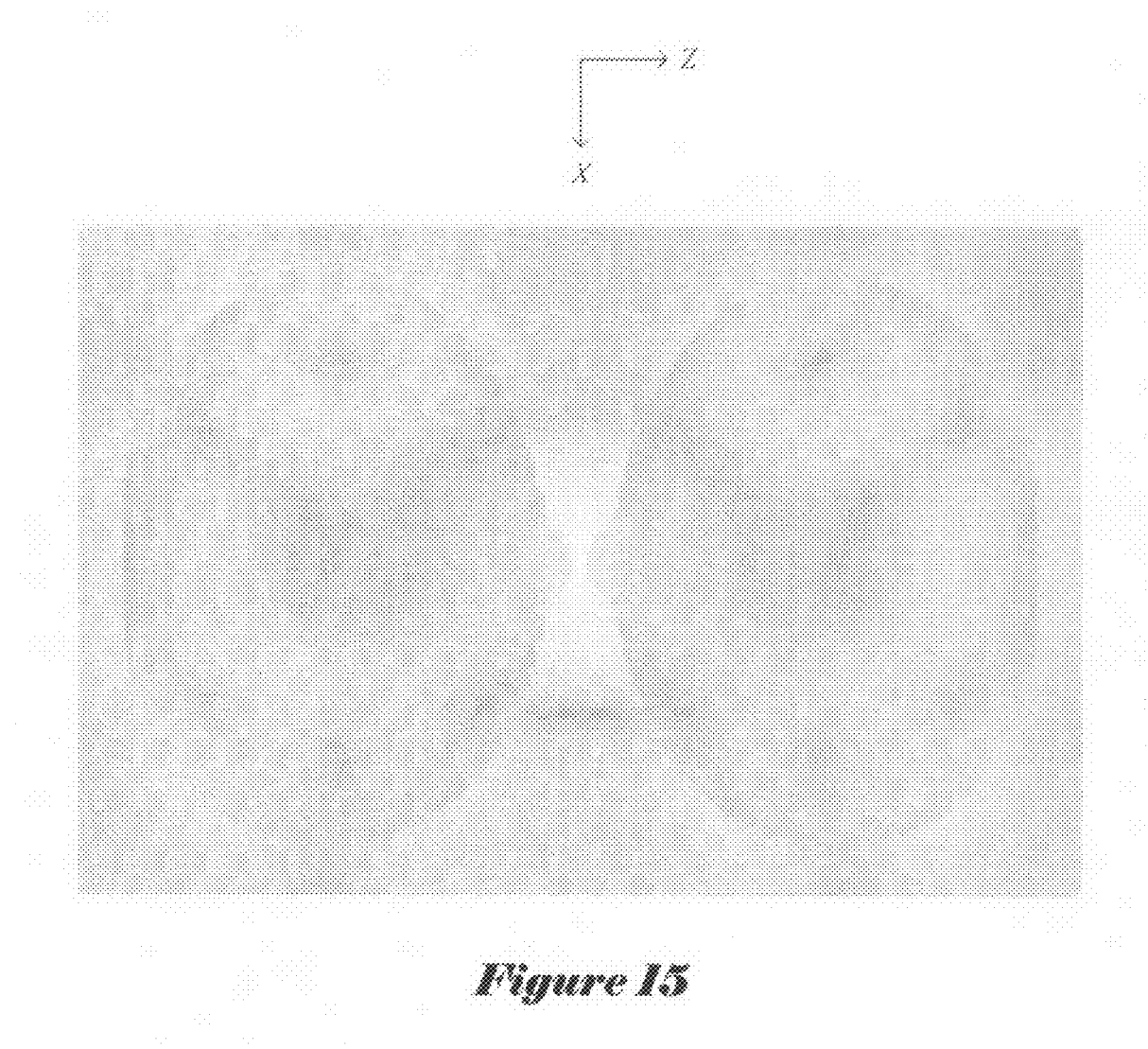

FIG. 15 shows two adjacent silicon disk structures, each of which has a relatively larger diameter silicon disk with a diameter of 2000 nm and a thickness of 200 nm. Each of the silicon disk structure also includes a relatively smaller silicon tip with a diameter of 12.5 nm and a thickness of 200 nm projecting from the larger silicon disk. The dielectric particle configuration shown in FIG. 15 is the same as the embodiment shown in FIG. 8. The spacing between the two adjacent smaller silicon disks is 30 nm. The silicon disks are surrounded by air having a lower index of refraction than that of the silicon disks. The silicon disks are irradiated with excitation EMR having a frequency of 121.197 THz, which is at or near a resonance frequency of each of the silicon disk structures. The wavevector of the excitation EMR is generally parallel to the Z axis shown in FIG. 15. The polarization direction of the electric field of the excitation EMR is generally parallel to the X axis shown in FIG. 15. The calculated intensity of the resonance modes confined within each of the silicon disk structures and the calculated intensity of the electric field between the adjacent relatively smaller silicon tips is shown in FIG. 15. As calculated, the maximum electric field intensity is located between the silicon disks and is about 113 times greater than an intensity of the electric field of the excitation EMR.

Although the present invention has been described in terms of particular embodiments, it is not intended that the present invention be limited to these embodiments. Modifications within the spirit of the present invention will be apparent to those skilled in the art. For example, the enhanced electric field between adjacent dielectric particles may be used to excite certain electronic states in a quantum dot. Accordingly, in another embodiment of the present invention, one or quantum dots may be formed over or on the two dielectric particles 102 and 103 shown in FIGS. 1 and 2 so that the enhanced electric field generated within or proximate the intermediate enhancement region 107 excites certain electronic states in the one or more quantum dots.

The foregoing description, for purposes of explanation, used specific nomenclature to provide a thorough understanding of the present invention. However, it will be apparent to one skilled in the art that the specific details are not required in order to practice the present invention. The foregoing descriptions of specific embodiments of the present invention are presented for purposes of illustration and description. They are not intended to be exhaustive of or to limit the present invention to the precise forms disclosed. Many modifications and variations are possible in view of the above teachings. The embodiments are shown and described in order to best explain the principles of the present invention and its practical applications, to thereby enable others skilled in the art to best utilize the present invention and various embodiments with various modifications as are suited to the particular use contemplated. It is intended that the scope of the present invention be defined by the claims and their equivalents:

The invention claimed is:

1. An electric-field-enhancement structure, comprising:
a substrate; and
an ordered arrangement of dielectric particles including at least two adjacent dielectric particles spaced from each other a controlled distance, the controlled distance selected so that when a resonance mode is excited in each of the at least two adjacent dielectric particles responsive to excitation electromagnetic radiation, each of the resonance modes interacts with each other to result in an enhanced electric field between the at least two adjacent dielectric particles, wherein each of the at least two adjacent dielectric particles comprises a body including a projection having a tip, the tip of each of the projections opposing each other and spaced from each other the controlled distance.

2. The electric-field-enhancement structure of claim 1 wherein the controlled distance is selected to maximize an intensity of the enhanced electric field between the at least two adjacent dielectric particles.

3. The electric-field-enhancement structure of claim 1 wherein the controlled distance is greater than zero.

4. The electric-field-enhancement structure of claim 1 wherein each of the at least two adjacent dielectric particles comprises one of:
a semiconductor material; and
an electrically insulating material.

5. The electric-field-enhancement structure of claim 1 wherein each of the at least two adjacent dielectric particles is configured as one of:
a circular disk;
a cylinder;
a triangular-shaped body; and
a rectangular-shaped body.

6. The electric-field-enhancement structure of claim 1 wherein each of the projections has a lateral dimension less than a lateral dimension of each of the bodies.

7. An electric-field-enhancement apparatus, comprising:
an excitation light source operable to output excitation electromagnetic radiation; and
an electric-field-enhancement structure including:
an ordered arrangement of dielectric particles including at least two adjacent dielectric particles spaced from each other a controlled distance, the controlled distance selected so that when a resonance mode is excited in each of the at least two adjacent dielectric particles responsive to the excitation electromagnetic radiation, each of the resonance modes interacts with each other to result in an enhanced electric field between the at least two adjacent dielectric particles, wherein each of the at least two adjacent dielectric articles comprises a body including a projection having a tip, the tip of each of the projections opposing each other and spaced from each other the controlled distance.

8. The electric-field-enhancement apparatus of claim 7 wherein:
the at least two adjacent dielectric particles are distributed along a first direction; and
the excitation light source is operable to output the excitation electromagnetic radiation with an electric field having a selected polarization direction and a selected wavevector, the selected polarization direction being generally parallel to the first direction.

9. The electric-field-enhancement apparatus of claim 8 wherein:
each of the at least two adjacent dielectric particles has a thickness defining a second direction that is generally perpendicular to the first direction; and
the selected wavevector of the excitation light is generally parallel to a third direction that is generally perpendicular to the first and second directions or the selected wavevector of the excitation light is generally parallel to the second direction.

10. The electric-field-enhancement apparatus of claim 8 wherein the excitation light source comprises a polarization structure configured to impart the selected polarization direction to the excitation light.

11. The electric-field-enhancement apparatus of claim 7 wherein the controlled distance is selected to maximize an intensity of the enhanced electric field between the at least two adjacent dielectric particles.

12. The electric-field-enhancement structure apparatus of claim 7 wherein the controlled distance is greater than zero.

13. The electric-field-enhancement apparatus of claim 7 wherein each of the at least two adjacent dielectric particles comprises one of:
- a semiconductor material; and
- an electrically insulating material.

14. The electric-field-enhancement apparatus of claim 7 wherein each of the at least two adjacent dielectric particles is configured as one of:
- a circular disk;
- a cylinder;
- a triangular-shaped body; and
- a rectangular-shaped body.

15. The electric-field-enhancement apparatus of claim 7 wherein each of the projections has a lateral dimension less than a lateral dimension of each of the bodies.

16. The electric-field-enhancement apparatus of claim 7, further comprising a detector configured to receive Raman-scattered light scattered by an analytc located adjacent to the dielectric particles.

17. A method of enhancing an electric field between at least two adjacent dielectric particles comprises a body including a projection having a tip, the tip of each of the projections opposing each other and spaced from each other the controlled distance the method comprising:
- irradiating the at least two adjacent dielectric particles with excitation electromagnetic radiation having a frequency selected to excite a resonance mode in each of the at least two adjacent dielectric particles, wherein the intensity of the resonance mode is greater in the projections than in the body of the nanoparticles; and
- positioning the at least two dielectric particles sufficiently close so that each of the resonance modes interacts with each other to result in an enhanced electric field between the at least two adjacent dielectric particles.

18. The method of claim 17 wherein:
- the at least two adjacent dielectric particles are distributed along a first direction; and
- irradiating the at least two adjacent dielectric particles with excitation electromagnetic radiation comprises selecting an electric field polarization direction of the excitation electromagnetic radiation to be generally parallel to the first direction.

* * * * *

UNITED STATES PATENT AND TRADEMARK OFFICE
CERTIFICATE OF CORRECTION

PATENT NO. : 7,696,477 B2
APPLICATION NO. : 11/724409
DATED : April 13, 2010
INVENTOR(S) : Mihail Sigalas et al.

It is certified that error appears in the above-identified patent and that said Letters Patent is hereby corrected as shown below:

On the Title page, in item (54), Title, in column 1, line 3, delete "APPARATUS" and insert -- APPARATUSES --, therefor.

In column 1, line 3, delete "APPARATUS" and insert -- APPARATUSES --, therefor.

In column 12, line 39, in Claim 7, delete "articles" and insert -- particles --, therefor.

In column 13, line 23, in Claim 16, delete "analytc" and insert -- analyte --, therefor.

In column 14, line 5, in Claim 17, delete "distance" and insert -- distance, --, therefor.

Signed and Sealed this

Twenty-third Day of November, 2010

David J. Kappos
*Director of the United States Patent and Trademark Office*